(12) United States Patent
Bellefeuille

(10) Patent No.: US 8,757,155 B2
(45) Date of Patent: Jun. 24, 2014

(54) AUTOMATIC SCAVENGER SYSTEM AND METHOD

(75) Inventor: Paul David Bellefeuille, Detroit Lakes, MN (US)

(73) Assignee: General Electric Company, Schenectady, NY (US)

(*) Notice: Subject to any disclaimer, the term of this patent is extended or adjusted under 35 U.S.C. 154(b) by 1387 days.

(21) Appl. No.: 11/674,285

(22) Filed: Feb. 13, 2007

(65) Prior Publication Data
US 2008/0190431 A1 Aug. 14, 2008

(51) Int. Cl.
*A62B 7/10* (2006.01)
*A61M 16/00* (2006.01)

(52) U.S. Cl.
USPC ............ 128/205.27; 128/204.18; 128/205.19

(58) Field of Classification Search
USPC ............ 128/200.24, 203.12–203.15, 203.25, 128/203.27–203.29, 204.18, 204.21, 128/205.12, 205.19, 205.24, 205.27, 128/207.14, 205.28, 914
See application file for complete search history.

(56) References Cited

U.S. PATENT DOCUMENTS

| | | | | |
|---|---|---|---|---|
| 5,735,267 A * | 4/1998 | Tobia | | 128/204.21 |
| 6,305,375 B1 * | 10/2001 | Brown | | 128/205.24 |
| 6,553,990 B2 * | 4/2003 | Hoffmann | | 128/203.12 |
| 6,745,764 B2 * | 6/2004 | Hickle | | 128/203.12 |
| 6,945,123 B1 | 9/2005 | Kuehl et al. | | |
| 7,178,524 B2 * | 2/2007 | Noble | | 128/206.11 |
| 7,503,323 B2 * | 3/2009 | Dalgetty et al. | | 128/203.15 |
| 7,596,965 B2 * | 10/2009 | Berry et al. | | 62/532 |
| 2004/0134493 A1 * | 7/2004 | McCombs et al. | | 128/202.26 |
| 2004/0200477 A1 * | 10/2004 | Bleys et al. | | 128/204.18 |
| 2006/0230931 A1 * | 10/2006 | Bliss et al. | | 95/130 |
| 2006/0254590 A1 * | 11/2006 | Berry et al. | | 128/205.12 |
| 2010/0147302 A1 * | 6/2010 | Selvarajan et al. | | 128/204.23 |

\* cited by examiner

*Primary Examiner* — Rachel Young
(74) *Attorney, Agent, or Firm* — Andrus Intellectual Property Law, LLP

(57) ABSTRACT

An anesthesia machine having an automatic scavenger system is disclosed herein. The anesthesia machine includes a scavenger hose configured to direct the transfer of an exhaled anesthetic agent from a patient, and a valve operatively connected to the scavenger hose. The valve is configured to selectively control the transmission of the exhaled anesthetic agent through the scavenger hose. The anesthesia machine also includes a switch operatively connected to the valve and to a controller. The switch is configured to link an operational status of the anesthesia machine with a position of the valve.

15 Claims, 2 Drawing Sheets

AUTOMATIC SCAVENGER SYSTEM AND METHOD

FIELD OF THE INVENTION

This disclosure relates generally to an automatic scavenger system for an anesthesia machine, and to a method for implementing the automatic scavenger system.

BACKGROUND OF THE INVENTION

Anesthesia may be administered to a patient in the form of a gas for purposes such as blocking the conscious perception of pain, producing unconsciousness, preventing memory formation, and/or preventing unwanted movement. The administered anesthesia is inhaled into the patient's lungs. Thereafter, the patient absorbs a fraction of the administered anesthesia and exhales the remainder. The exhaled anesthetic gas is preferably collected in a manner adapted to minimize the potential for unintended exposure to the anesthetic agent. Scavenger systems have therefore been developed to facilitate the collection and disposal of the exhaled anesthetic gas.

Scavenger systems can be coupled with a compressor that is adapted to generate a low-pressure region and thereby transfer the exhaled anesthetic gas. The exhaled anesthetic agent is generally passed from the patient through an exhaust vent and thereafter becomes diluted with outside air to the extent that it is no longer dangerous. The compressor may be selectively coupled to the scavenger system with a valve. This valve is manually opened to draw exhaled anesthetic agent through the scavenger system, and is manually closed to shut off the scavenger system. One problem with such a manually operated valve is that it is prone to human error and may, for example, lead to excessive compressor operation or insufficient compressor operation.

If, for example, the scavenger system compressor is not implemented while anesthesia is being administered to a patient, anesthetic gas exhaled from the patient can pose a health risk to nearby personnel. Conversely, if the scavenger system compressor is implemented during periods wherein exhaled anesthesia is not being collected (e.g., when the anesthesia machine is off), the compressor is unnecessarily burdened which can diminish compressor reliability and lifespan.

BRIEF DESCRIPTION OF THE INVENTION

The above-mentioned shortcomings, disadvantages and problems are addressed herein which will be understood by reading and understanding the following specification.

In an embodiment, an anesthesia machine includes a scavenger hose configured to direct the transfer of an exhaled anesthetic agent from a patient, and a valve operatively connected to the scavenger hose. The valve is configured to selectively control the transmission of the exhaled anesthetic agent through the scavenger hose. The anesthesia machine also includes a switch operatively connected to the valve and to a controller. The switch is configured to link an operational status of the anesthesia machine with a position of the valve.

In another embodiment, an anesthesia system includes an anesthesia machine comprising a scavenger assembly, a scavenger hose connected to the scavenger assembly, and a valve operatively connected to the scavenger hose. The valve has a first position wherein the scavenger hose is at least partially open and a second position wherein the scavenger hose is generally occluded. The anesthesia machine also includes a switch operatively connected to the valve. The switch is configured to link the status of the anesthesia machine with the position of the valve such that the scavenger assembly is automatically activated when the anesthesia machine is turned on and the scavenger assembly is automatically deactivated when the anesthesia machine is turned off. The anesthesia system also includes a compressor operatively connected to the scavenger hose, and an exhaust line operatively connected to the compressor. The exhaust line is configured to direct an exhaled anesthetic agent to an exhaust vent.

In another embodiment, a method for implementing an anesthesia machine having an automatic scavenger system includes connecting a scavenger hose to a compressor, and providing a valve operatively connected to the scavenger hose. The valve has a first position wherein the scavenger hose is at least partially open and a second position wherein the scavenger hose is generally occluded. The method also includes providing a switch operatively connected to the valve. The switch is configured to link the operational status of the anesthesia machine with the position of the valve. The method also includes implementing the switch to select an operational status of the anesthesia machine such that the valve is automatically set to a corresponding valve position.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
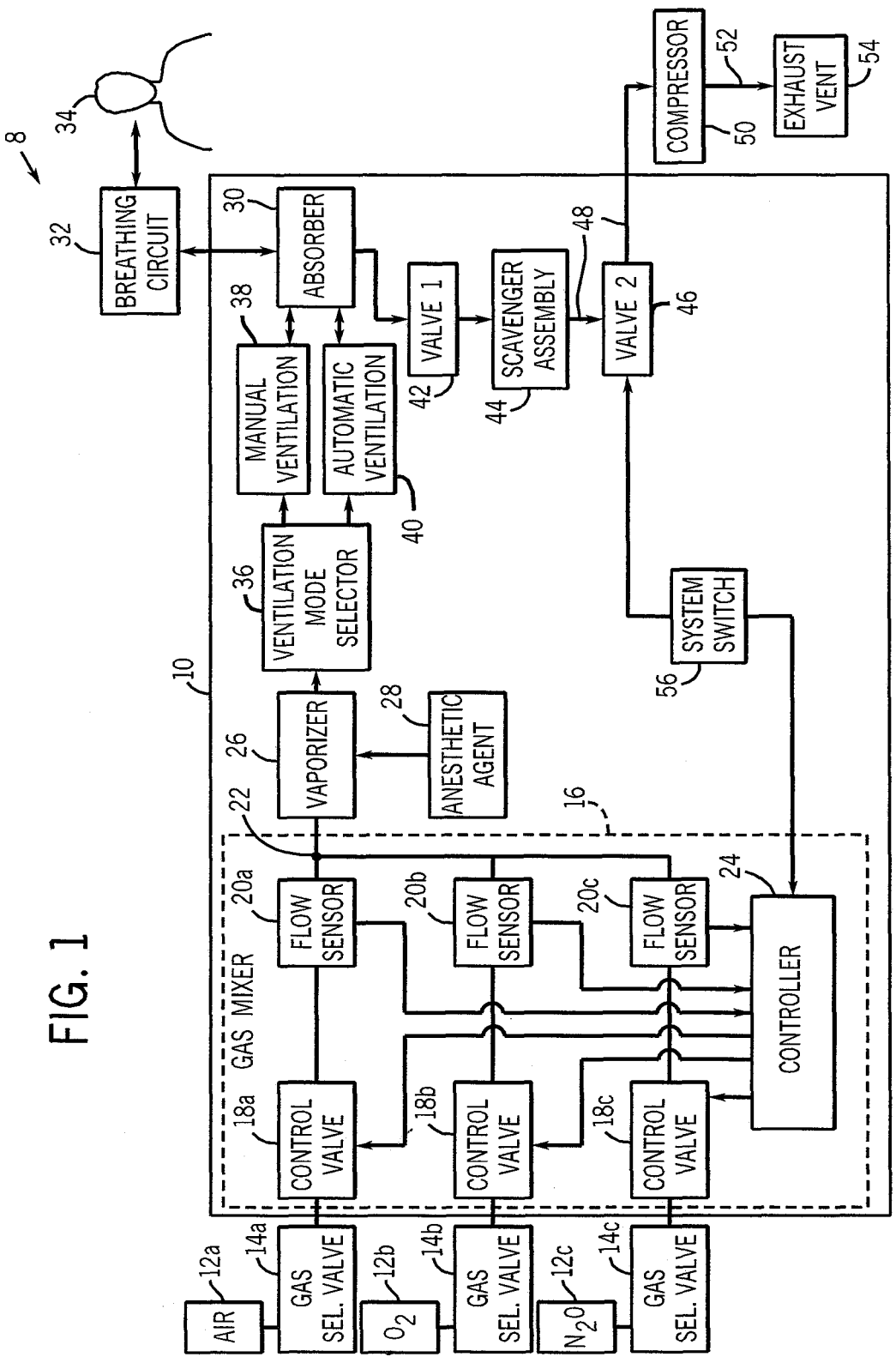
FIG. 1 is a schematic diagram illustrating an anesthesia machine and scavenger system in accordance with an embodiment.

Referring to FIG. 1, an anesthesia system 8 is schematically depicted in accordance with an embodiment. The anesthesia system 8 includes an anesthesia machine 10, a plurality of gas storage devices 12a, 12b and 12c, a compressor 50, and an exhaust vent 54. The anesthesia machine 10 is shown for illustrative purposes and it should be appreciated that other types of anesthesia machines may alternately be implemented. In a typical hospital environment, the gas storage devices 12a, 12b and 12c are centrally located storage tanks configured to supply medical gas to multiple anesthesia machines and multiple hospital rooms. This is exemplarily depicted in FIG. 2. The storage tanks are generally pressurized to facilitate the transfer of the medical gas to the anesthesia machine 10.

The gas storage devices 12a, 12b and 12c will hereinafter be described as including an air tank 12a, an oxygen ($O_2$) tank 12b, and a nitrous oxide ($N_2O$) tank 12c, respectively, however it should be appreciated that other storage devices and other types of gas may alternatively be implemented. The gas storage tanks 12a, 12b and 12c are each connected to one of the gas selector valves 14a, 14b, and 14c, respectively. The gas selector valves 14a, 14b and 14c may be implemented to shut off the flow of medical gas from the storage tanks 12a, 12b and 12c when the anesthesia machine 10 is not operational. When one of the gas selector valves 14a, 14b and 14c is opened, gas from a respective storage tank 12a, 12b and 12c is transferred under pressure to the anesthesia machine 10.

The anesthesia machine 10 includes a gas mixer 16 adapted to receive medical gas from the storage tanks 12a, 12b and 12c. The gas mixer 16 includes a plurality of control valves 18a, 18b and 18c that are respectively connected to one of the gas selector valves 14a, 14b and 14c. The gas mixer 16 also includes a plurality of flow sensors 20a, 20b and 20c that are each disposed downstream from a respective control valve 18a, 18b, and 18c. After passing through one of the control valves 18a, 18b and 18c, and passing by one of the flow sensors 20a, 20b and 20c, the individual gasses (i.e., air, $O_2$ and $N_2O$) are combined to form a mixed gas at the mixed gas outlet 22.

The control valves 18a, 18b and 18c and the flow sensors 20a, 20b and 20c are each connected to a controller 24. The controller 24 is configured to operate the control valves 18a, 18b and 18c in a response to gas flow rate feedback from the sensors 20a, 20b and 20c. Accordingly, the controller 24 can be implemented to maintain a selectable flow rate for each gas (i.e., air, $O_2$ and $N_2O$) such that the mixed gas at the mixed gas outlet 22 comprises a selectable ratio of air, $O_2$ and $N_2O$. The mixed gas flows to a vaporizer 26 where an anesthetic agent 28 is vaporized and added to the mixed gas from the mixed gas outlet 22. The anesthetic agent 28 and mixed gas combination passes through an absorber 30, enters the breathing circuit 32 and is delivered to the patient 34.

According to one embodiment, the anesthesia machine 10 includes a ventilation mode selector 36, a manual ventilation device 38 and an automatic ventilation device 40 operatively connected between the vaporizer 26 and the absorber 30. The ventilation mode selector 36 is operable to select either the manual ventilation device 38 or the automatic ventilation device 40. The manual ventilation device 38 generally includes a breathing bag or ventilation bag (not shown) that can be manually squeezed to ventilate the patient 34. The automatic ventilation device 40 is a known device configured to automatically ventilate the patient 34.

A fraction of the anesthetic agent 28 administered to the patient 34 is absorbed, and the remainder is expelled as the patient 34 exhales. The exhaled anesthetic agent 28 is transferred via the breathing circuit 32 to the absorber 30. A portion of the exhaled anesthetic agent 28 can be re-cycled as a cost savings measure, and the remainder of the exhaled anesthetic agent 28 is transferred from the absorber 30, through the scavenger assembly 44, and out the exhaust vent 54 as will be described in detail hereinafter.

Figure 2:
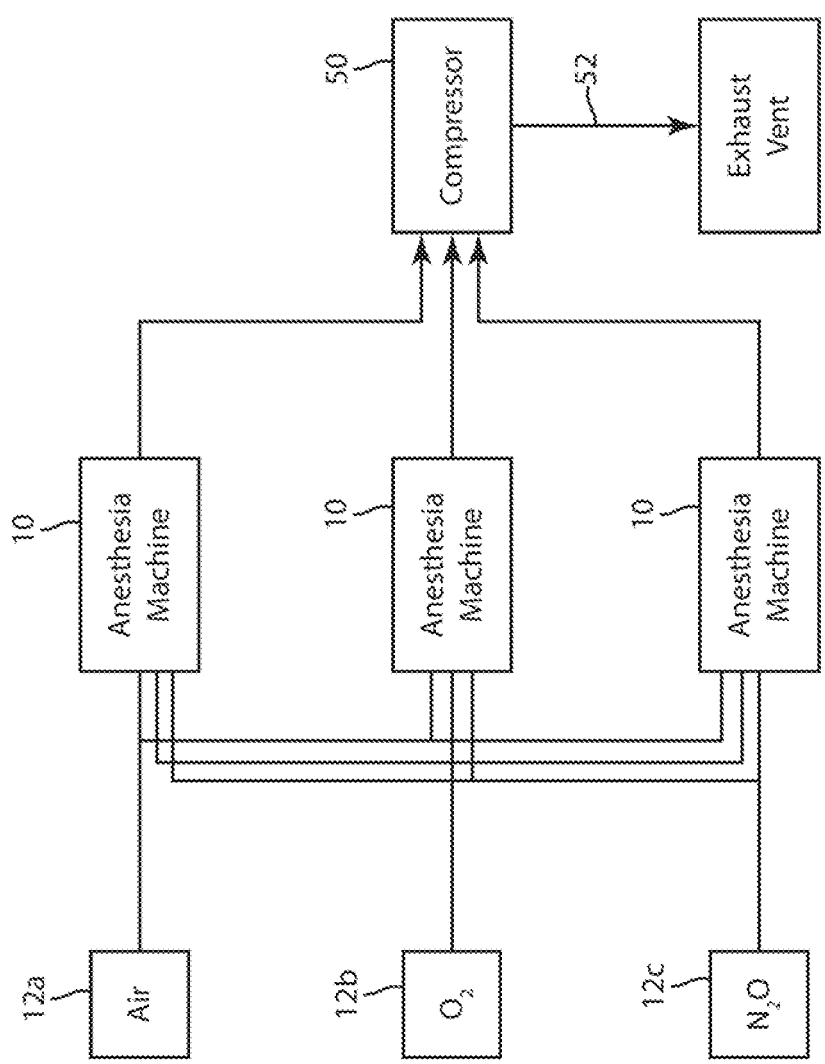
FIG. 2 is a schematic diagram illustrating a system of a plurality of anesthesia machines and a scavenger system in accordance with an embodiment.

A first valve 42 may be operatively connected to an inlet portion of the scavenger assembly 44, and a second valve 46 may be operatively connected to an outlet portion of the scavenger assembly 44. A scavenger hose 48 couples the scavenger assembly 44 with a compressor 50. According to one embodiment, as depicted in FIG. 2, the compressor 50 is centrally located and supports multiple anesthesia machines in a manner similar to that previously described with respect to the storage tanks 12a, 12b and 12c. When the scavenger hose 48 is connected to the compressor 50, and both valves 42, 46 are at least partially open, the compressor 50 creates a partial vacuum or region of low pressure adapted to transfer the exhaled anesthetic agent 28 from the absorber 30, through an exhaust line 52, and out the exhaust vent 54. After passing out through the exhaust vent 54, the exhaled anesthetic agent 28 is generally released into the atmosphere where it becomes diluted with outside air to the extent that it is no longer dangerous.

According to an embodiment, the first valve 42 is a variably adjustable valve that can be opened by a selectable amount to control the rate at which exhaled anesthetic agent 28 is drawn from the absorber 30. Thereafter, the first valve 42 is generally maintained at a fully open or partially open position to enable automatic operation of the scavenger assembly 44. It should be appreciated that the first valve 42 is optional and may not be incorporated in all anesthesia machines. According to an embodiment, the second valve 46 is a pneumatically actuated closed-bias valve. For purposes of this disclosure, a "pneumatically actuated closed-bias valve" is a valve designed to remain closed unless a pneumatic pressure is introduced. It should, however, be appreciated that the valves 42 and 46 may include any known device adapted to selectively regulate fluid flow.

A system switch or power switch 56 is operatively connected to the controller 24 and the second valve 46. The system switch 56 is configured to link the position of the second valve 46 (i.e., either open or closed) with the status of the anesthesia machine 10 (i.e., either on or off). For purpose of this disclosure, the "status of an anesthesia machine" refers to whether the anesthesia machine is on (i.e., powered-up) or off (i.e., powered-down), and the "position of a valve" or the "valve position" refers to the degree to which the valve is open or closed.

According to one embodiment, the system switch 56 is operable to turn-on or power-up the anesthesia machine 10 and to generally simultaneously open the second valve 46. As an example, the system switch 56 may transmit an electronic signal to the controller 24 in order to power-up the anesthesia machine 10, and generally simultaneously transfer a gas such as oxygen or air to pneumatically open the second valve 46. Similarly, the system switch 56 may be adapted to turn-off or power-down the anesthesia machine 10, and to generally simultaneously close the second valve 46.

Linking the position of the second valve 46 with the status of the anesthesia machine 10 ensures that the scavenger assembly 44 remains operational whenever the anesthesia machine 10 is on. This substantially reduces the potential for a situation wherein hospital personnel are exposed to a high concentration of exhaled anesthetic agent. Linking the position of the second valve 46 with the status of the anesthesia machine 10 also ensures that the scavenger assembly 44 remains de-coupled from the compressor 50 whenever the anesthesia machine 10 is off. This minimizes the burden or load applied to the compressor 50 during periods of anesthesia machine inactivity.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

I claim:

1. An anesthesia machine comprising:
   a controller;
   a scavenger hose configured to direct exhaled anesthetic agent from a patient and configured to pneumatically connect to a compressor that creates at least a partial vacuum to draw the exhaled anesthetic agent through the scavenger hose;

a valve operatively connected to the scavenger hose, said valve configured to allow the transmission of the exhaled anesthetic agent through the scavenger hose in a first position and occlude the scavenger hose in a second position;

a switch operatively connected to the valve and to said controller, said switch being configured to automatically turn on the anesthesia machine and cause the valve to operate such that the valve is in the first position when the switch is in a first state and automatically turn off the anesthesia machine and cause the valve to operate such that the valve is in the second position when the switch is in a second state; and a scavenger assembly operatively connected between the patient and the scavenger hose, wherein movement of the valve to the first position activates the scavenger assembly;

wherein the position of the valve between the first position and second position corresponds to the state of the switch between the first state and the second state.

2. The anesthesia machine of claim 1, wherein said valve is a pneumatically actuated closed-bias valve, and the switch operates to transfer gas to the valve independently of the exhaled anesthetic agent to operate the valve between the first position and the second position.

3. The anesthesia machine of claim 1, further comprising an absorber operatively connected to the scavenger assembly, said absorber configured to collect the exhaled anesthetic agent from the patient.

4. The anesthesia machine of claim 1, further comprising a variably adjustable valve operatively connected to the scavenger assembly.

5. The anesthesia machine of claim 4, wherein the variably adjustable valve can be opened by a selectable amount to control the rate at which the exhaled anesthetic agent is transferable through the scavenger assembly.

6. An anesthesia system comprising:
a first anesthesia machine comprising:
a first scavenger assembly;
a first scavenger hose connected to the first scavenger assembly;
a first valve operatively connected to the first scavenger hose, said first valve having a first position wherein the first scavenger hose is at least partially open and a second position wherein the first scavenger hose is occluded; and
a first switch operatively connected to the first valve, said first switch transmits an electronic signal to turn on the first anesthesia machine and the first valve is moved into the first position when the first switch is in a first state and the first anesthesia machine is turned off and the first valve is in the second position when the first switch is in a second state;
a compressor operatively connected to the first scavenger assembly through the first valve, the compressor operates independently of the state of the first switch to generate at least a partial vacuum wherein when the first valve is in the first position an exhaled anesthetic agent is drawn into the first scavenger assembly by the at least partial vacuum, activating the first scavenger assembly and when the first valve is in the second position the first scavenger assembly is decoupled from the compressor, deactivating the first scavenger assembly; and
an exhaust line operatively connected to the compressor, said exhaust line configured to direct the exhaled anesthetic agent out an exhaust vent.

7. The anesthesia system of claim 6, further comprising a first absorber operatively connected to the first scavenger assembly.

8. The anesthesia system of claim 6, further comprising a first variably adjustable valve operatively connected to the first scavenger assembly.

9. The anesthesia system of claim 8, wherein said first variably adjustable valve can be opened by a selectable amount to control the rate at which the exhaled anesthetic agent is transferable through the first scavenger assembly.

10. A method for implementing an anesthesia machine having an automatic scavenger system comprising:
connecting a scavenger hose between a scavenger assembly and a compressor;
providing a valve operatively connected to the scavenger hose, said valve having a first position wherein the scavenger hose is at least partially open and a second position wherein the scavenger hose is occluded;
providing a switch operatively connected to the valve, said switch being movable between a first state to turn on the anesthesia machine and move the valve to the first position and a second state to turn off the anesthesia machine and move the valve to the second position;
selectively operating the switch to select an operational status of the anesthesia machine such that the valve is automatically set to a corresponding valve position;
automatically activating the scavenger assembly upon moving the valve into the first position; and
operating the compressor independently of a state of the switch to create at least a partial vacuum, and the partial vacuum draws exhaled anesthetic agent through the scavenger hose when the valve is in the first position.

11. The method of claim 10, wherein said providing a valve includes providing a pneumatically actuated closed-bias valve.

12. The method of claim 10, further comprising providing a variably adjustable valve operatively connected to the scavenger assembly.

13. The method of claim 12, further comprising setting the variably adjustable valve to an at least partially open position before said implementing the switch.

14. The anesthetic system of claim 6, further comprising a second anesthesia machine comprising:
a second scavenger assembly;
a second scavenger hose connected to the second scavenger assembly and to the compressor;
a second valve operatively connected to the second scavenger hose, said second valve having a first position wherein the second scavenger hose is at least partially open and a second position wherein the second scavenger hose is occluded; and
a second switch operatively connected to the second valve, said second switch being configured to link the status of the second anesthesia machine with the position of the second valve such that the second scavenger assembly is automatically activated, the second anesthesia machine is automatically turned on, and the second valve is in the first position when the second switch is in a first state and the second scavenger assembly is automatically deactivated, the second anesthesia machine is turned off, and the second valve is in the second position when the second switch is in a second state;
wherein the compressor generates the at least partial vacuum for the first anesthesia machine and the second anesthesia machine, and the decoupling of the first scavenger assembly or the second scavenger from the compressor by the first valve or the second valve in the second position when the first switch or the second switch is in the second state reduces loading on the compressor when at least one of the first anesthesia machine or second anesthesia machine is off.

15. The system of claim 14, wherein the first scavenger assembly or the second scavenger assembly are activated by connection to the at least partial vacuum provided by the compressor through the first valve or the second valve operating in the first position.

\* \* \* \* \*